US012674874B2

(12) United States Patent
Coviello et al.

(10) Patent No.: US 12,674,874 B2
(45) Date of Patent: Jul. 7, 2026

(54) PASSIVE ACOUSTIC MAPPING USING COMPRESSIVE SENSING

(71) Applicant: OXSONICS LIMITED, Oxford (GB)

(72) Inventors: Christian M. Coviello, Oxford (GB); Calum J. Crake, Oxford (GB); Richard J. Kozick, Danville, PA (US)

(73) Assignee: OXSONICS LIMITED, Oxford (GB)

( * ) Notice: Subject to any disclaimer, the term of this patent is extended or adjusted under 35 U.S.C. 154(b) by 269 days.

(21) Appl. No.: 18/253,052

(22) PCT Filed: Nov. 16, 2021

(86) PCT No.: PCT/GB2021/052957
§ 371 (c)(1),
(2) Date: May 16, 2023

(87) PCT Pub. No.: WO2022/101645
PCT Pub. Date: May 19, 2022

(65) Prior Publication Data
US 2024/0019561 A1        Jan. 18, 2024

(30) Foreign Application Priority Data

Nov. 16, 2020    (GB) ..................................... 2017979

(51) Int. Cl.
*G01S 7/52*        (2006.01)
*A61N 7/02*        (2006.01)
*G01S 15/89*        (2006.01)

(52) U.S. Cl.
CPC ............ *G01S 7/52036* (2013.01); *A61N 7/02* (2013.01); *G01S 15/8915* (2013.01)

(58) Field of Classification Search
None
See application file for complete search history.

(56) References Cited

U.S. PATENT DOCUMENTS

2018/0284249 A1*   10/2018   Schretter ............. G01S 15/8915

FOREIGN PATENT DOCUMENTS

CN        109998589 A      7/2019
EP        3088912 A1      11/2016
(Continued)

OTHER PUBLICATIONS

Ackermann, Dimitri, and Georg Schmitz. "Detection and tracking of multiple microbubbles in ultrasound B-mode images." IEEE transactions on ultrasonics, ferroelectrics, and frequency control 63.1 (2015): 72-82. (Year: 2015).*

(Continued)

*Primary Examiner* — Jonathan D Armstrong
(74) *Attorney, Agent, or Firm* — William J. Clemens; Shumaker, Loop & Kendrick, LLP

(57)        ABSTRACT

A passive compression wave imaging system for locating cavitation bubbles, the system comprising a plurality of sensor elements (202b) arranged in an array and each arranged to produce an output signal, and processing means (204a, 204b) arranged to: define a sample period, and a sample space over which the signal can be sampled at each of a plurality of sample points in the sample space; define a grid of candidate bubble positions; define a random projection identifying a respective different group of the sample points for each of the output signals; sample each of the output signals at the group of sample points defined by the random projection to generate sample data; define a diction-ary which defines the sample values that would be obtained for the signal of each of the respective group of sensor elements at each of the sample points for the sample period for a bubble at each of the candidate bubble positions; define a vector the elements of which identify the candidate bubble positions; and perform a minimisation operation to derive the vector element values, and hence the bubble positions, from the sample data, the basis and the random projection.

20 Claims, 7 Drawing Sheets

(56) References Cited

FOREIGN PATENT DOCUMENTS

| WO | 2005094701 A1 | 10/2005 |
| WO | 2010052494 A1 | 5/2010 |
| WO | 2014041370 A1 | 3/2014 |
| WO | 2016067253 A1 | 5/2016 |
| WO | 2019224350 A1 | 11/2019 |

OTHER PUBLICATIONS

Kim, Jihun, et al. "Compressed sensing-based super-resolution ultrasound imaging for faster acquisition and high quality images." IEEE Transactions on Biomedical Engineering 68.11 (2021): 3317-3326. (Year: 2021).*

Ali Cafer Gurbuz, et al., Bearing Estimation via Spatial Sparsity using Compressive Sensing, IEEE Transactions on Aerospace and Electronic Systems, Apr. 2012, pp. 1358-1369, vol. 48, No. 2, IEEE Service Center, Piscataway, NJ, US.

Gya Ngy Miklass, et al., Passive Cavitation Mapping with Temporal Sparsity Constraint, The Journal of the Acoustical Society of America, Nov. 2011, pp. 3489-3497, vol. 130, No. 5, American Institute of Physics for the Acoustical Society of America, New York, NY, US.

United Kingdom Search Report dated Aug. 19, 2021.

* cited by examiner

Fig. 2
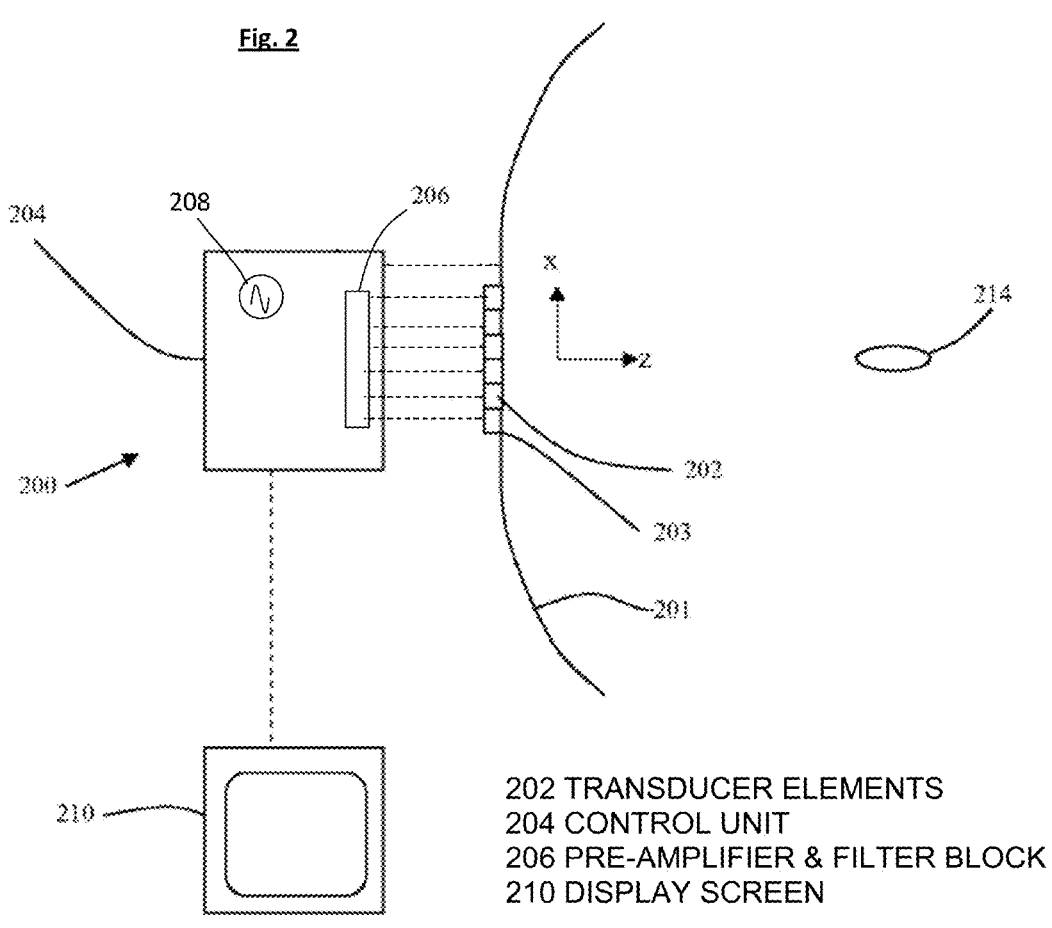
202 TRANSDUCER ELEMENTS
204 CONTROL UNIT
206 PRE-AMPLIFIER & FILTER BLOCK
210 DISPLAY SCREEN
202 TRANSDUCER ELEMENTS
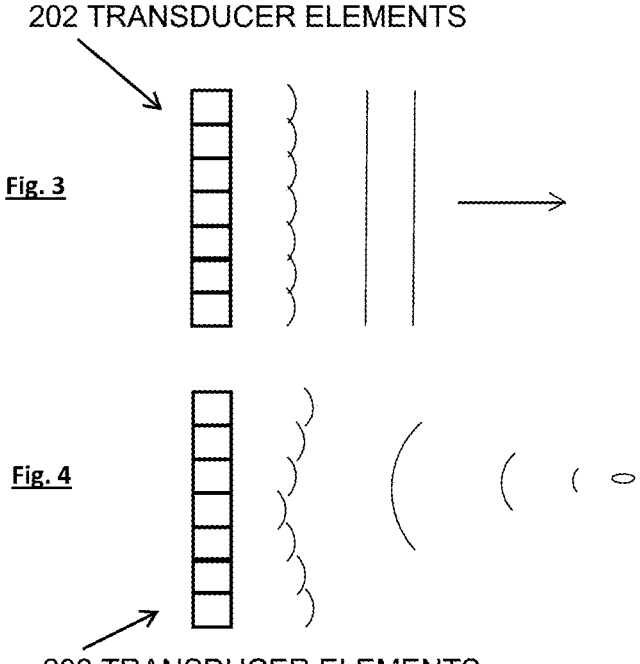
Fig. 3
Fig. 4
202 TRANSDUCER ELEMENTS

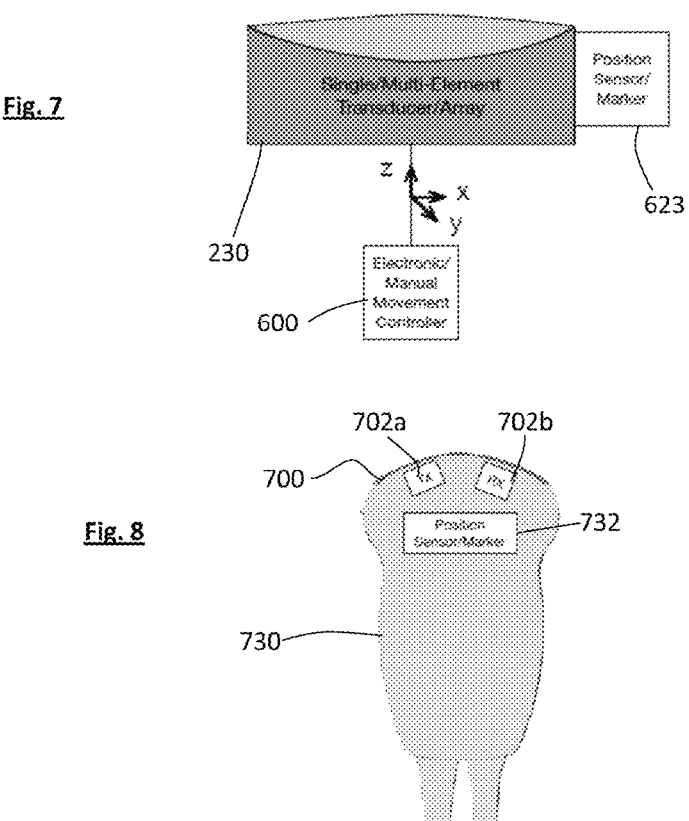
Fig. 7
Fig. 8
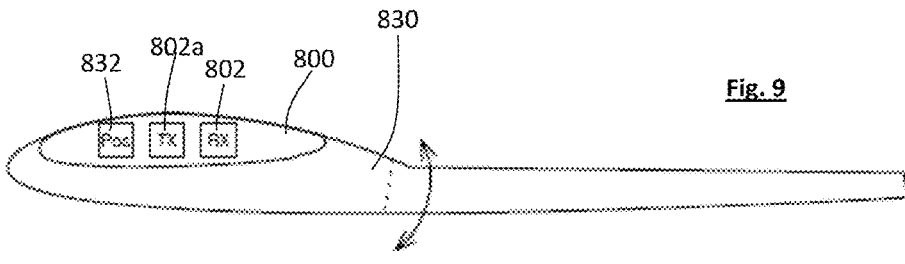
Fig. 9
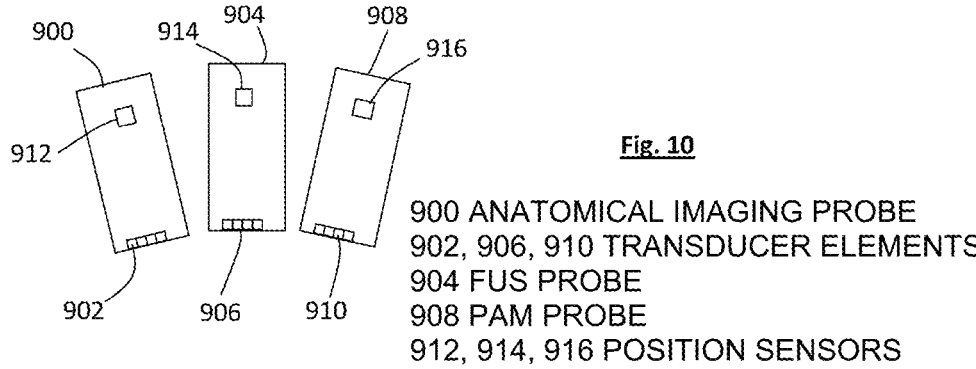
Fig. 10
900 ANATOMICAL IMAGING PROBE
902, 906, 910 TRANSDUCER ELEMENTS
904 FUS PROBE
908 PAM PROBE
912, 914, 916 POSITION SENSORS

PASSIVE ACOUSTIC MAPPING USING COMPRESSIVE SENSING

FIELD OF THE INVENTION

The invention relates to passive acoustic mapping and in particular to passive ultrasound imaging of cavitation, for example in medical ultrasound systems.

BACKGROUND TO THE INVENTION

Real-time treatment monitoring of therapeutic ultrasound, i.e. the determination of both the spatial extent and dose of the therapy, is a key issue for widespread clinical adoption, whether the application is high-intensity focused ultrasound (HIFU) ablation of cancerous tissue or ultrasound-enhanced targeted drug delivery. One method of achieving this is passive acoustic mapping (PAM), also referred to as passive cavitation mapping (PCM) or passive cavitation imaging (PCI). PAM is a technique that allows imaging of bubble activity without knowledge of the time of flight of the interrogating pulse causing the bubble activity. The technique has been used in various applications of therapeutic ultrasound such as monitoring of cavitation-enhanced drug delivery, thermal ablation of soft tissue and transcranial therapies. Examples of such systems are described in WO2010/052494A1 which describes fundamental methods of PAM and WO2014/041370A1 which describes methods of PAM using sparse transducer arrays.

Since its original development, PAM has been widely studied and techniques such as optimal beamforming, planar-projection and non-Gaussian signal processing demonstrated to improve resolution or processing speed. However, while hardware developments such as high channel-count ultrasound research platforms provide unprecedented data capture ability, real-time processing of the growing data stream presents an evolving challenge.

Compressive sensing relies on the fact that many practical signals are sparse in some domain, and thus may be sampled significantly below the Nyquist rate and subsequently reconstructed via an optimization process (R. G. Baraniuk, "Compressive Sensing [Lecture Notes]," IEEE Signal Processing Magazine, vol. 24, no. 4, pp. 118-121, July 2007, doi: 10.1109/MSP.2007.4286571.) The technique has been widely studied in applications such as radar (R. Baraniuk and P. Steeghs, "Compressive Radar Imaging," in 2007 IEEE Radar Conference, April 2007, pp. 128-133, doi: 10.1109/RADAR.2007.374203.), MRI (M. Lustig, D. L. Donoho, J. M. Santos, and J. M. Pauly, "Compressed Sensing MRI," IEEE Signal Processing Magazine, vol. 25, no. 2, pp. 72-82, March 2008, doi: 10.1109/MSP.2007.914728.) and conventional diagnostic ultrasound imaging Previous work has applied sparse array processing techniques to PAM including matching and basis pursuit (M. Gyöngy and C. M. Coviello, "Passive cavitation mapping with temporal sparsity constraint," The Journal of the Acoustical Society of America, vol. 130, no. 5, pp. 3489-3497, November 2011, doi: 10.1121/1.3626138.) co-array processing (C. M. Coviello, R. J. Kozick, A. Hurrell, P. P. Smith, and C. Coussios, "Thin-film sparse boundary array design for passive acoustic mapping during ultrasound therapy," IEEE Transactions on Ultrasonics, Ferroelectrics, and Frequency Control, vol. 59, no. 10, pp. 2322-2330, October 2012, doi: 10.1109/TUFFC.2012.2457.), and PAM based upon sparse reconstruction of radiofrequency data and sparse selection of array elements (C. Crake et al., "Passive acoustic mapping and B-mode ultrasound imaging utilizing compressed sensing for real-time monitoring of cavitation-enhanced drug delivery," The Journal of the Acoustical Society of America, vol. 143, no. 3, Art. no. 3, March 2018, doi: 10.1121/1.5036143).

SUMMARY OF THE INVENTION

The present invention provides a system in which PAM operates directly on sparsely sampled data, which may be referred to as compressive-sensing PAM (CS-PAM).

The present invention provides a passive compression wave imaging system for locating cavitation bubbles, the system comprising a plurality of sensor elements arranged in an array and each arranged to produce an output signal, and processing means arranged to: define a sample period, and a sample space over which the signal can be sampled at each of a plurality of sample points in the sample space; define a grid of candidate bubble positions; define a random projection identifying a respective different group of the sample points for each of the output signals; sample each of the output signals at the group of sample points defined by the random projection to generate sample data; define a dictionary which defines the sample values that would be obtained for the signal of each of the sensor elements at each of the respective group of sample points for the sample period for a bubble at each of the candidate bubble positions; define a vector the elements of which identify the candidate bubble positions; and perform a minimisation operation to derive the vector element values, and hence the bubble positions, from the sample data, the basis and the random projection.

The vector defining the candidate bubble positions may be the same for all sensor elements, or it may be defined separately for each of the sensor elements.

The random projection may be defined by at least one random projection matrix, which may be one random projection matrix defined as a plurality of sub-matrices, or two or more random projection matrices each of which defines at least one stage of compression.

The sample period may be a period for which one static image is to be generated. If the system is arranged to generate video images then the sample period is determined by the frame rate of the video.

The sample space may be time. The processing means may be further arranged to define a sample rate that defines the sample points as a plurality of sample times within the sample period at which samples can be taken.

The sample space may be frequency. The processing means may be further arranged to define the sample points as a plurality of sample frequencies at which samples can be taken. The processing means may be arranged to separate out an analogue component of the sensor output signals at each of the frequency sample points, and to sample each of the components for the sample period.

If the sample space is time, the processing means may be arranged to sample each of the sensor output signals, and to determine frequency component samples for each of the output signals from the time domain samples.

The processing means may be arranged to form linear combinations of the sample data from the sensors thereby to form virtual sensor data corresponding to each of a plurality of virtual sensors.

The random projection matrix may be further arranged to define the linear combinations. Alternatively the linear combinations may be defined by a further matrix.

The processing means may be arranged to identify one of the sensor elements as a reference sensor element. The processing means may be arranged to sample the output signal from the reference sensor element at each of the sample points to generate reference data. The processing means may be arranged to define a delay time for each combination of one of the candidate bubble positions and one of the senor elements. The processing means may be arranged to determine the dictionary from the reference data and the delay times.

The present invention further provides a method of passive compression wave imaging of cavitation bubbles, the method comprising: defining a sample period, and a plurality of sample points over a sample space; defining a grid of candidate bubble positions; defining a random projection identifying a respective different group of the sample points for each of the output signals; sampling each of the output signals at the group of sample points defined by the random projection to generate sample data; defining a dictionary which defines sample values that would be obtained for a signal of each of the respective group of sensor elements at each of the sample points for the sample period for a bubble at each of the candidate bubble positions; defining a vector the elements of which identify the candidate bubble positions; and performing a minimisation operation to derive the vector element values, and hence the bubble positions, from the sample data, the basis and the random projection.

The present invention may therefore provide compressive sensing (CS) techniques which can be used to perform PAM using sparsely sampled data, which may improve image quality and processing speed for a given set of data.

The system may further comprise, in any combination, any one or more features of the preferred embodiments of the invention which will now be described by way of example only with reference to the accompanying drawings.

BRIEF DESCRIPTION OF THE DRAWINGS

FIG. 2 is a schematic diagram of an imaging system according to an embodiment of the invention;

FIG. 3 is a diagram showing the generation of plane acoustic waves from the system of FIG. 2;

FIG. 4 is a diagram showing the generation of focused acoustic waves from the system of FIG. 2;

FIG. 7 is a schematic diagram of an embodiment of the invention having a mechanically controlled transducer array;

FIG. 8 is a schematic diagram of an embodiment of the invention having a handheld transducer array;

FIG. 9 is a schematic diagram of an embodiment of the invention having an internal probe in which the transducer array is mounted;

FIG. 10 is a schematic diagram of an embodiment of the invention in which different transducer arrays are mounted on separate modules;

DESCRIPTION OF EMBODIMENTS OF THE INVENTION

Figure 1:
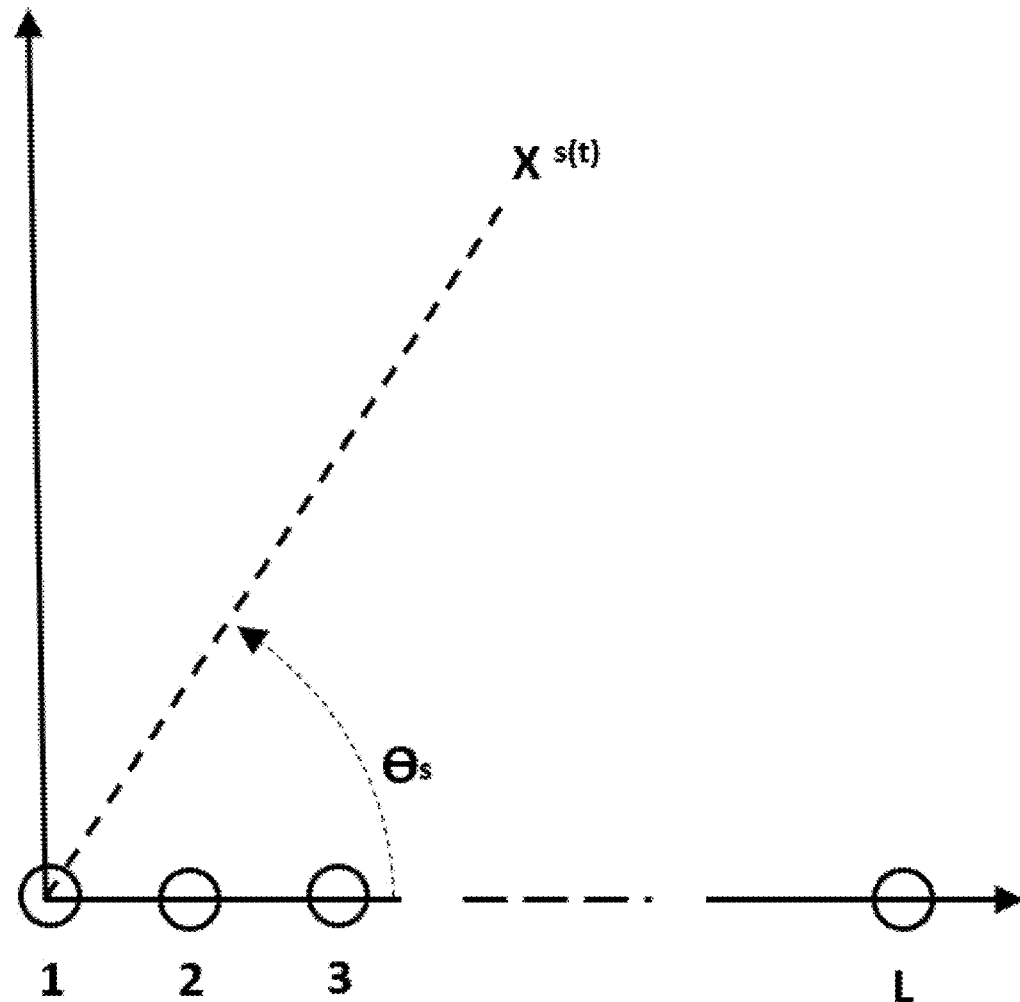
FIG. 1 is a schematic diagram of a sensor array forming part of an embodiment of the invention.

First the basic method of compressive sensing will be described. Consider without loss of generality the case of a single far-field acoustic source propagating from a position marked as 'x' towards a linear array of i={1,2, . . . ,L} receiving elements, or sensors, as shown in FIG. 1. Consider the signal recorded at sensor i to be:

$$\xi_i(t) = w \cdot s\big(t + \Delta_i(\theta_s) - R/c\big), \qquad (1)$$

where w is a sensor factor, for example indicating the conversion factor from received acoustic signal, detected as a varying pressure, to the electrical signal output as a varying electrical voltage, s is the signal produced at the source, R is the range, i.e. distance, from the array origin to the source, c is the speed of sound between the source and the sensor, $\theta_s$ is the arrival angle for acoustic waves from the source to the array origin (defined as the position of sensor 1 in FIG. 1), measured relative to the line (or plane) through the sensor array, and $\Delta_i(\theta_s)$ is the relative time delay at sensor i. The relative time delay is parameterized by angle of arrival as $$\Delta_i(\theta_s) = \frac{1}{c}\begin{bmatrix} x_i & y_i & 0 \end{bmatrix}\begin{bmatrix} \cos\theta_s \\ \sin\theta_s \\ 0 \end{bmatrix} \qquad (2)$$

since $\theta_s$ is assumed to be constant over all sensors for the far-field case.

If each sensor signal is digitized with sampling frequency $$F_s = 1/T_s$$

for $N_t$ samples over a sampling period, then the signal at each array element can be represented by $$\xi_i(t) = \begin{bmatrix} w \cdot s\big(t_o + \Delta_i(\theta_s) = R/c\big) \\ w \cdot s\big(t_o + T_s + \Delta_i(\theta_s) = R/c\big) \\ \vdots \\ w \cdot s\big(t_o + (N_t - 1)T_s + \Delta_i(\theta_s) = R/c\big) \end{bmatrix} \qquad (3)$$

Next, we introduce an angle space grid which contains all possible angles at which the source could be located, defined by B={$\theta_1$ $\theta_2$ . . . $\theta_N$}, with N defining the size and resolution of the grid, and the sparsity pattern vector b which selects from the angle space grid the actual source angle(s). The sparsity pattern vector b therefore only has non-zero entries at the indices at which lie the grid angles that are to be selected. It can be related to the received data as $$\xi_i = \Psi_i b \qquad (4)$$

where $\Psi_i$ is a sparsity basis defining the sample values for all sensor elements at each of the sample times for all possible source angles. The j-th column of the sparsity basis $\Psi_i$ is defined as the vector $$[\Psi_i]_j = \begin{bmatrix} w \cdot s(t_o + \Delta_i(\theta_j) - R/c) \\ \vdots \\ w \cdot s(t_{N-1} + \Delta_i(\theta_j) - R/c) \end{bmatrix} \quad (5)$$

and here the index $N_t$ is to signify an arbitrary number of samples and j is the index of possible source angles.

The problem in this context is to recover the sparse vector b (and hence the angle of the true source) from compressed measurements. Rather than measuring every signal at every sample time, to reduce the data we measure M samples or 'compressive measurements' per sensor by taking linear projections with M random vectors to yield the model $$\beta_i = \Phi_i \xi_i = \Phi_i \Psi_i b, \, i = 1, \dots, L \quad (6)$$

where here the ($M \times N_t$) random projection matrix $\Phi_i$ is defined by $$\Phi_i = \begin{bmatrix} (\phi_i^1)^T \\ \vdots \\ (\phi_i^M)^T \end{bmatrix} \quad (7)$$

and each row $$(\phi_i^m)^T$$

for m=1, . . . , M is a random (e.g. independent identically distributed Bernoulli or Gaussian) row vector, defining a random group of the sample times selected from all of the sample times in the sample period, for each of the array elements. The particular choice of $\Phi_i$ is to ensure small mutual correlation with $\Psi_i$.

The goal is to solve from the ($L \times M$) measurements, where L is the number of sensors and M is the number of samples taken of the signal from each of the sensors, for b, such that the arrival angle is found. The $\ell_1$ minimization problem to solve is then written as $$\hat{b} = \text{argmin} \|b\|_1, \text{ subject to } \Phi\Psi b = \beta, \quad (8)$$

$$\text{where } \Phi = \text{diag}\{\Phi_1, \dots, \Phi_L\}, \, \Psi = [\Psi_1, \dots, \Psi_L], \text{ and}$$

$$\beta = [\beta_1, \dots, \beta_L].$$

However, if the source signal s is unknown then the $\ell_1$ minimization cannot be constructed in the same way. In this case, if we assume that the true source signal s has been recorded in the sampled sensor data at each of the sensors, then one of the sensors can be chosen as the reference sensor to be normally sampled at Nyquist rate.

Compressed Sensing PAM

To adapt the concept of compressed sensing far field beamforming to PAM, which is a near field imaging method, instead of an angle space grid, a voxel space grid is defined. Assume initially that we have a single known bubble at a particular defined voxel (defined, for 2D imaging with a linear sensor array along the x axis, on a transverse-axial or x-z grid) with coordinates $r_s=[x_s, z_s]$, which yields a signal model for sensor i of $$\xi_i(t) = w_i/(4\pi \cdot |r_i - r_s|) \cdot p\left(t - \frac{|r_i - r_s|}{c}\right), \quad (9)$$

Where p is the acoustic pressure at the source s, $w_i$ is the piezoelectric efficiency of the sensor element, $r_i=[x_i, z_i]$ is the sensor location and $1/(4\pi \cdot |r_i - r_s|)$ accounts for spherical spreading. Let $\alpha_i = w_i/(4\pi \cdot |r_i - r_s|)$, and then as previously in equation (3), if we sample this received data we arrive, for each sensor, at $$\xi_i = \begin{bmatrix} \xi_i(t_0) \\ \xi_i(t_0 + T_s) \\ \vdots \\ \xi_i(t_0 + (N_t - 1)T_s) \end{bmatrix} = \begin{bmatrix} \alpha_i \cdot p\left(t_0 - \frac{|r_i - r_s|}{c}\right) \\ \alpha_i \cdot p\left(t_0 + T_S - \frac{|r_i - r_s|}{c}\right) \\ \vdots \\ \alpha_i \cdot p\left(t_0 + (N_t - 1)T_S - \frac{|r_i - r_s|}{c}\right) \end{bmatrix}. \quad (10)$$

Now assume a sparse grid B of voxel positions (where voxel and pixel are synonymous depending on whether the system is imaging in 2D or 3D respectively) determined by a defined voxel grid $[x_{min}, z_{min}] \times [x_{max}, z_{max}]$ by $$B = \{\rho_1 \, \rho_2 \, \dots \, \rho_N\}, \quad (11)$$

where N ultimately defines the resolution of the grid. If the true source is included in the grid, i.e. the source voxel position $r_s$ appears in the grid as one of the $\rho_j$ candidate positions, then the position should be recoverable using the same methodology. Similarly to the far field method described above, let b be the sparsity pattern vector, which is related to the received data by $$\xi_i = \Psi_i b, \quad (12)$$

where again $\Psi_i$ is the sparsity basis for each sensor i=1, . . . , L, whose j-th column is a vector defined by $$[\Psi_i]_j = \begin{bmatrix} \alpha_{i,j} \cdot p\left(t_0 - \frac{|r_i - \rho_j|}{c}\right) \\ \vdots \\ \alpha_i \cdot p\left(t_0 + (N_t - 1)T_S - \frac{|r_i - \rho_j|}{c}\right) \end{bmatrix}, \quad (13)$$

where j identifies a particular voxel location corresponding to index $j \in \{1, \dots, N\}$ in the grid and $\alpha_{i,j}=w_i/(4\pi \cdot |r_i - \rho_j|)$ for each sensor i=1, . . . , L.

The CS-PAM problem is to recover $r_s$, and so we proceed by measuring random samples as linear projections from each of the sensor signals. This provides a form equivalent to equations (6) to (8), but where b provides a sparse vector of likely voxel positions. The projections are fully described below.

One item to note is that the formulation assumes a known bubble, and not multiple unknown bubbles. If there are multiple bubbles, the formulation holds provided there is limited mutual coherence between individual bubbles. Similarly to the beamforming example, since the bubble signal is unknown, then a reference sensor must be used that is sampled and recorded at the Nyquist rate, as described next.

In practice the bubble signal as a function of time p(t) is unknown so the basis cannot be defined as in (13). In this case we follow the approach in A. C. Gurbuz, V. Cevher, and J. H. Mcclellan, "Bearing Estimation via Spatial Sparsity using Compressive Sensing," IEEE Transactions on Aerospace and Electronic Systems, vol. 48, no. 2, pp. 1358-1369, 2012, doi: 10.1109/TAES.2012.6178067 and choose a reference sensor (RS) with index $i_{RS} \in \{1, \ldots, N\}$, then let $\xi_{i_{RS}}(t)$ denote the signal measured at the RS. The basis is formed by scaling and time-shifting the full-rate samples of the RS as follows:

$$
[\Psi_i]_j = \frac{w_i |r_{i_{RS}} - \rho_j|}{w_{i_{RS}} |r_i - \rho_j|} \times \begin{bmatrix} \xi_{i_{RS}}\left(t_0 + \frac{|r_{i_{RS}} - \rho_j| - |r_i - \rho_j|}{c}\right) \\ \vdots \\ \xi_{i_{RS}}\left(t_0 + (N_t - 1)T_S + \frac{|r_{i_{RS}} - \rho_j||r_i - \rho_j|}{c}\right) \end{bmatrix}. \tag{14}
$$

The rationale for this approach is that if the sensor data is noise-free from a single bubble as in (9), and if the grid in (11) includes the source location (i.e., $\rho_j = r_s$ for an index j), then using (14) in (12) leads to a sparse solution vector b with a single nonzero element at index j for all sensors i=1, . . . , L excluding the RS. For the RS with i=$i_{RS}$, all of the columns of $[\Psi_{i_{RS}}]_j$ for j=1, . . . , N are identical and equal to the samples of the RS signal, so the RS is excluded when solving for the sparse solution vector.

CS-PAM in Frequency Domain

The time delays of the RS signal required to form the dictionary basis vectors in (14) may be obtained efficiently in the frequency domain, as will now be described. The system may also use a two-level compressed sampling method over frequency bins and sensor data, which corresponds to linear projections (i.e. compressed sampling) over space and time. The CS-PAM image is then obtained directly from the compressed data.

The discrete Fourier transform (DFT) of the sampled sensor data $\xi_i(t_0)$, $\xi_i(t_0+T_S)$, . . . , $\xi_i(t_0+(N_t-1)T_S)$ is defined as $$
\Xi_i\left(k \cdot \frac{F_s}{N_f}\right) = \sum_{n=0}^{N_t-1} \xi_i(t_0 + nT_s)\exp\left(-j2\pi(nT_s)\left(k\frac{F_s}{N_f}\right)\right) = \tag{15}
$$

$$
\sum_{n=0}^{N_t-1} \xi_i(t_0 + nT_s)\exp\left(-j\frac{2\pi}{N_f}nk\right),
$$

For frequency bin index k=0, . . . , $N_f$−1 and sensor index i=1, . . . , L
where the number of frequency bins $N_f \geq N_t$ is usually chosen as an integer power of 2 so that the DFT is efficiently computed with the fast Fourier transform (FFT) algorithm. The DFT frequency bin values are integer multiples of $F_s/N_f$ Hz, and since the sensor data is real-valued, only $$
\frac{N_f}{2} + 1
$$

of the values are unique, with $$
\Xi_i\left((N_f - k) \cdot \frac{F_s}{N_f}\right) = \Xi_i^*\left(k \cdot \frac{F_s}{N_f}\right)
$$

for k=1, . . . , $N_f/2$−1 where * denotes complex conjugate. The DFT bins with indices k=0 and k=$N_f/2$ are excluded (these are the components at DC and the Nyquist frequency for sampling rate $F_S$ samples/sec). In general, additional frequency bins may be excluded to achieve a filtering effect, such as to account for the frequency response of the sensors, band-stop filtering in frequency intervals around harmonics of the HIFU insonification pulses, or other objectives. After this filtering, let $N_b \leq N_f/2$−1 denote the number of frequency bins that are retained for each sensor. Also let $\mathcal{N}$ denote the subset of DFT indices from $\{1, \ldots, N_f/2-1\}$ that correspond to the retained frequency bins, with elements of this set denoted by $\mathcal{N} = \{b_1, \ldots, b_{N_b}\}$. Then the retained frequencies in Hz are $$
f_k = b_k \frac{F_s}{N_f}
$$

for k=1, . . . , $N_b$. Finally, define the complex-valued, frequency domain samples of the filtered sensor data as the vectors $\Xi_i$ for i=1, . . . , L, each with dimension $N_b$ and elements $$
\Xi_i\left(b_k \cdot \frac{F_s}{N_f}\right)
$$

from (15) for k=1, . . . , $N_b$. These vectors are used for subsequent processing to produce the CS-PAM image.

Next we form the counterpart to the dictionary basis vectors in (14) in the frequency domain. We use the same notation $\Psi_i$ for the frequency domain dictionary basis vectors, but now the matrix for each sensor i=1, . . . , L is complex-valued with dimension $N_b \times N$. The frequency domain RS data is in the vector $\Xi_{i_{RS}}$ with elements $[\Xi_{i_{RS}}]_k$ for k=1, . . . , $N_b$, then the elements in the frequency domain dictionary matrices are given by $$
[\Psi_i]_{k,j} = \frac{w_i |r_{i_{RS}} - \rho_j|}{w_{i_{RS}} |r_i - \rho_j|}[\Xi_{i_{RS}}]_k \exp\left(j2\pi f_k \frac{|r_{i_{RS}} - \rho_j| - |r_i - \rho_j|}{c}\right) \tag{16}
$$

where $f_k$ are the frequency components retained after filtering in Hz and i$\in \{1, \ldots, L\}$ and i$\neq i_{RS}$, k=1, . . . , $N_b$, j=1, . . . , N. Then similar to (4), the columns of $\Psi_i$ provide a basis in which the frequency domain sensor data is described by a sparse vector b with nonzero elements at indices that correspond to bubble locations, $$
\Xi_i = \Psi_i b, i \in \{1, \ldots, L\} \text{ and } i \neq i_{RS}. \tag{17}
$$

The objective in CS-PAM is to recover b from compressed data. As explained in the previous section, the RS is excluded in (17) because (16) with i=$i_{RS}$ is a matrix with identical columns, each equal to $\Xi_{i_{RS}}$.

The compressed sampling (CS) is performed in two steps. First the data for each sensor is reduced from $N_b$ complex frequency samples to $M_F \leq N_b$ real frequency samples. Then the data is compressed over the sensors from L to $M_L \leq L$ values, resulting in a total of M=$M_F$ $M_L$ real-valued compressed samples. The compression over sensors is performed by multiple linear combinations of the compressed data from each of the sensors. Each linear combination has random coefficients, and this produces virtual sensor data corresponding to (compressed) data from a smaller number of virtual sensors. The linear combinations are the same for each possible bubble position This results in a compressed dictionary basis A'$_i$ for each sensor. The overall compression ratio relative to the N$_t$ time domain samples at each sensor, including the reduction by frequency domain filtering, is $$\text{Compression ratio} = \frac{M_F M_L}{N_t L} = \frac{M}{N_t L} \qquad (18)$$

We have found that CS-PAM images can be formed using only a few percent of the original data.

The compression over frequency bins is performed with $(M_F \times N_b)$ frequency compression matrices $\Phi'_i$ with complex-valued, independent, identically distributed (iid) elements to yield the compressed sensor data $\beta'_i$ and the compressed dictionary matrices A'$_i$ that make up the compressed dictionary, $$\beta'_i = \text{Re}\{\Phi'_i \Xi_i\} \ (M_F \times 1) \qquad (19)$$

$$A'_i = \text{Re}\{\Phi'_i \Psi_i\} \ (M_F \times N), \ i \in \{1, \ldots, L\}, \ i \neq i_{RS}$$

where Re$\{\cdot\}$ is the real part. The real part arises because in order to equate the result with a corresponding compression in the time domain, the DFT frequency bins at frequencies in the range $(F_S/2, F_S)$ must be compressed with corresponding complex conjugate weights, and including these terms in the linear combination produces the real part in (19).

The compression over sensors is performed with a $(M_L \times (L-1))$ sensor compression matrix $\Phi$ with real-valued, iid elements $\phi_{m,i}$ to yield $$\beta_m = \sum_{\substack{i \in \{1, \ldots, L\}, \\ i \neq i_{RS}}} \phi_{m,i} \beta'_i (M_F \times 1) \qquad (20)$$

$$A_m = \sum_{\substack{i \in \{1, \ldots, L\}, \\ i \neq i_{RS}}} \phi_{m,i} A'_i (M_F \times N), \ m = 1, \ldots, M_L$$

Then similar to (8) the $\ell_1$ minimization problem to solve is $$\hat{b} = \text{argmin} \|b\|_1, \text{ subject to } \beta = Ab \qquad (21)$$

where $$A = \begin{bmatrix} A_1 \\ \vdots \\ A_{M_L} \end{bmatrix} \text{ and } \beta = \begin{bmatrix} \beta_1 \\ \vdots \\ \beta_{M_L} \end{bmatrix}.$$

The sparse solution vector $\hat{b}$, defining which of the grid of source positions contains a source, is used to produce the CS-PAM image by plotting the values of $\hat{b}$ on the voxel grid $B = \{\rho_1 \ \rho_2 \ldots \rho_N\}$ in (11). In order to account for noise in the sensor data and other model mismatches, the following problem is solved instead, $$\hat{b} = \text{argmin} \|b\|_1, \text{ subject to } \|\beta - A \ b\|_2 < \epsilon. \qquad (22)$$

where $\epsilon$ is an error value.

A further example of a random projection matrix, and therefore the method used by the processing means, for performing the two-stage compression by a single matrix, will now be described.

Define vectors $\Xi'_i$ for i=1, ..., L containing the frequency domain data from all sensors with elements $$\Xi_i \left( b_k \cdot \frac{F_s}{N_f} \right)$$

for all frequency bins k=1, ..., N$_f$/2−1. Then define $\Phi''_i$ as matrices with dimension $(M_F \times (N_f/2-1))$ similar to the complex-valued, random matrices $\Phi'_i$ in (19), with the columns of $\Phi'_i$ placed in columns $\mathcal{N} = \{b_1, \ldots, b_{N_b}\}$ of $\Phi''_i$, and the other columns of $\Phi''_i$ are zeros to perform filtering of selected frequency bins. Then similarly define augmented dictionary basis vector matrices $\Psi'_i$ similarly to (16), with more rows so the dimension is $((N_f/2-1) \times N)$, where $f_k$ in (16) is replaced by $$k \cdot \frac{F_s}{N_f}$$

and k=1, ..., N$_f$/2−1. Then (19) is equivalent to $$\beta'_i = \text{Re}\{\Phi''_i \Xi'_i\} \ (M_F \times 1) \qquad (23)$$

$$A'_i = \text{Re}\{\Phi''_i \Psi'_i\} \ (M_F \times N)$$

where the compression and filtering over frequency bins is performed by the projection matrices $\Phi''_i$. Then we form a real-valued matrix $\Phi'$ with dimension $(M_L \times L)$ that contains the columns of $\Phi$ (whose elements $\phi_{m,i}$ appear in (20)) with an additional column of zeros inserted at column i$_{RS}$ corresponding to the index of the reference sensor. The projection matrix $\Phi'$ performs the compression over sensors, and the elements of $\Phi'$ are denoted $\phi'_{m,i}$.

The matrix A and vector $\beta$ in (21) that correspond to the compressed dictionary and compressed sensor data, respectively, can be formed by a single projection matrix $\phi_T$ as follows. First define $$\Xi' = \begin{bmatrix} \Xi'_1 \\ \vdots \\ \Xi'_L \end{bmatrix} \text{ and } \Psi' = \begin{bmatrix} \Psi'_1 \\ \vdots \\ \Psi'_L \end{bmatrix} \qquad (24)$$

Then $$\beta = \text{Re}\{\phi_T \Xi'\} \text{ and } A = \text{Re}\{\phi_T \Psi'\} \qquad (25)$$

where the blocks in $\phi_T$ are defined by $$\phi_T = \begin{bmatrix} \phi'_{1,1} \Phi''_1 & \cdots & \phi'_{1,L} \Phi''_L \\ \vdots & \ddots & \vdots \\ \phi'_{M_L,1} \Phi''_1 & \cdots & \phi'_{M_L,L} \Phi''_L \end{bmatrix} \qquad (26)$$

The structure of $\phi_T$ shows that the $\Phi''_i$ perform compression over the frequency bins for each sensor i=1, . . . , L, and then each row of the $\Phi'$ matrix contains the coefficients of the linear combination that performs compression over the sensors. The expression in (26) performs the two stages of compression with a single projection matrix.

The RS must be sampled at the full Nyquist rate in order to form the dictionary matrices in (16) and the matrix A from (19)-(21). However, the compressed samples from the other sensors in $\beta_m$ in (20) can be obtained directly from the continuous-time sensor signals $\xi_i(t)$ observed over the time interval t∈[t$_0$, t$_0$+T] where the observation time, or sample period, is T=N$_t$ T$_s$. The matrices $\Phi'_i$ in (19) have dimension $(M_F{\times}N_b)$, so we augment these with columns of zeros to form $\Phi''_i$ with dimension $(M_F{\times}(N_t/2-1))$. The columns of $\Phi'_i$ are placed in columns $\mathcal{N}_b$={b$_1$, . . . , b$_{N_b}$} of $\Phi''_i$, and the other columns of $\Phi''_i$ are zeros. Then we form the inverse FFT of each row of $\Phi''_i$ to form the matrices $\Phi''_i$ containing real-valued time samples, and then each row is interpolated to form the continuous-time functions $\phi''_{m,i}(t)$ for m=1, . . . , $M_F$. Then the compressed samples in (19) are obtained as $$[\beta'_i]_m = \int_0^T \xi_i(t+t_0) \, \phi''_{m,i}(t) \, dt \qquad (27)$$

$$m = 1, \ldots, M_F, i \in \{1, \ldots, L\}$$

$$i \neq i_{RS}$$

with no need for full Nyquist rate sampling of the sensor signals other than the RS.

Multiple Measurement Vector (MMV) Formulation

The CS-PAM method described above can be referred to as a Single Measurement Vector (SMV) formulation, because the compressed measurements from all sensors and frequency bins are stacked into the vector β defined after (21), and the compressed dictionary is correspondingly stacked into the matrix A defined after (21). The linear model β=A b in (21) has N total unknowns in the vector b (although the sparse solution $\hat{b}$ to (22) has many fewer than N nonzero entries) and $M_F{\cdot}M_L$ measurements in β, so β=A b is a set of $M_F{\cdot}M_L$ equations. Recall that N is the number of voxels in the grid defined in (11) and $M_F$, $M_L$ characterizes the compression over frequency bins and sensors, respectively. Sparse recovery algorithms for solving (22) typically assume that the model β=A b is underdetermined (fewer equations than unknowns), which requires $M_F{\cdot}M_L$<N. Meeting this condition may require excessive compression, and furthermore the model $\Xi_i{=}\Psi_i b$ in (17) implies that the same b vector describes the data $\Xi_i$ at each sensor in terms of the dictionary basis $\Psi_i$ for that sensor, which may be overly restrictive. A multiple measurement vector (MMV) formulation of CS-PAM addresses both of these concerns and is described next. The MMV formulation was not considered in the prior work in A. C. Gurbuz, V. Cevher, and J. H. Mcclellan, "Bearing Estimation via Spatial Sparsity using Compressive Sensing," IEEE Transactions on Aerospace and Electronic Systems, vol. 48, no. 2, pp. 1358-1369, 2012, doi: 10.1109/TAES.2012.6178067.

The MMV formulation modifies (17) to include a different vector b$_i$ at each sensor, $$\Xi_i = \Psi_i b_i, i \in \{1, \ldots, L\} \text{ and } i \neq i_{RS}. \qquad (28)$$

Each of the b$_i$ vectors are sparse with nonzero elements at the same locations, indicating the voxel positions where energy is emitted. The standard MMV model in compressive sensing uses the same dictionary $\Psi$ at each sensor, so the model in (28) is termed a generalized MMV (GMMV) since each sensor has a different dictionary matrix defined by (16). Compression of the measurements and dictionary matrices over frequency bins is performed as in (19) to yield the following GMMV model for the compressed data, $$\beta'_i = A'_i b_i, i \in \{1, \ldots, L\} \text{ and } i \neq i_{RS}. \qquad (29)$$

These equations for each sensor are underdetermined when $M_F$<N, which is easier to achieve than for the SMV model. No compression over sensors is performed in the GMMV formulation, so the processing in (20) is omitted. This is because with a fixed or limited number of sensors, there is only a modest reduction in compression over sensors possible. In contrast, for bubble imaging most of the compression can be achieved over the frequency bins. Then the generalization of the $\ell_1$ minimization problem in (22) is $$b_i, \min_{i \in \{1, \ldots, L\}, i \neq i_{RS}} \sum_{m=1}^{M_F} \left( \sum_{i \in \{1, \ldots, L\}, i \neq i_{RS}} |[b_i]_m|^2 \right)^{1/2} \qquad (30)$$

$$\text{subject to } \sum_{i \in \{1, \ldots, L\}, i \neq i_{RS}} \|\beta'_i - A'_i b_i\|_2^2 < \epsilon^2$$

Computationally efficient algorithms for solving (30) are given in (L. Li, X. Huang, J. A. K. Suykens, "Signal recovery for jointly sparse vectors with different sensing matrices," Signal Processing, Volume 108, 2015, Pages 451-458, ISSN 0165-1684, https://doi.org/10.1016/j.sigpro.2014.10.010) and (R. Heckel and H. Bolcskei, "Joint sparsity with different measurement matrices," 2012 50th Annual Allerton Conference on Communication, Control, and Computing (Allerton), 2012, pp. 698-702, doi: 10.1109/Allerton.2012.6483286). The GMMV formulation can also be viewed as a block-sparse model as discussed in (Y. C. Eldar, P. Kuppinger, and H. Bolcskei, "Block-sparse signals: Uncertainty relations and efficient recovery," IEEE Trans. Signal Process., vol. 58, no. 6, pp. 3042-3054, 2010). The GMMV problem in (30) reduces to the SMV problem in (22) when b$_i$=b.

Methods for Determining Voxel Grid Resolution and CS Parameters

The spacing (or resolution) of the voxel grid in (11) must be chosen appropriately. If the spacing is too large, then the basis dictionary cannot adequately model the sensor measurements and sources are missed in the CS-PAM image. If the spacing is too small, then the dictionary basis has large coherence which limits the number of distinct sources that can be recovered in the CS-PAM image. This section describes a method for choosing an appropriate resolution of the voxel grid in the lateral and axial directions.

Consider one source at voxel position r$_s$ in the region of interest [x$_{min}$, z$_{min}$] [x$_{max}$, z$_{max}$]. Assume that p(t) is the time waveform emitted by the source. If the sensor element positions are r$_i$ for i=1, . . . , L then the time-delayed waveforms at the sensors are $$p\left(t - \frac{|r_i - r_s|}{c}\right),$$

where spherical spreading and scaling factors are omitted in this discussion. If p(t) is sampled over a measurement interval then let $\Xi$ be the vector of DFT values with dimension $N_b$ after removing certain frequency bins, as described in the paragraph after (15). Then the DFT vectors $\Xi_i$ at each sensor have elements that are phase-shifted as $$[\Xi_i]_k = [\Xi]_k \cdot \exp\left(-j2\pi f_k \frac{|r_i - r_s|}{c}\right), \ k = 1, \dots, N_b \qquad (31)$$

Next we form a set of dictionary basis vectors $\Psi_i(\rho)$ for each sensor i on a set of voxel locations $\rho$ that are densely sampled (with small grid spacing) over a region in the neighborhood of the source location $r_s$. If the reference sensor index is $i_{RS}$, then following (16) with scaling factors omitted, these dictionary vectors have elements $$[\Psi_i]_k(\rho) = [\Xi]_k \exp\left(-j2\pi f_k \frac{|r_i - \rho| - |r_{i_{RS}} - \rho| + |r_{i_{RS}} - r_s|}{c}\right) \qquad (32)$$

Then the following inner product assesses the match between the sensor data in (31) and the dictionary basis vectors for voxel locations p in the neighborhood of the source location:

$$f(\rho) = \sum_{i \in \{1, \dots, L\}, i \neq i_{RS}} \mathrm{Re}\left(\Xi_i^H \Psi_i(\rho)\right) = \sum_{i \in \{1, \dots, L\}, i \neq i_{RS}} \sum_{k=1}^{N_b} \qquad (33)$$

$$|[\Xi]_k|^2 \cos\left(2\pi f_k \frac{|r_i - \rho| - |r_{i_{RS}} - \rho| + |r_{i_{RS}} - r_s| - |r_i - r_s|}{c}\right)$$

The inner product (33) achieves the maximum value at the source location $\rho = r_s$, with $$f(r_s) = \sum_{i \in \{1, \dots, L\}, i \neq i_{RS}} \sum_{k=1}^{N_b} |[\Xi_i]_k|^2$$

and $f(\rho) \leq f(r_s)$ for all other voxel locations. The function $f(\rho)$ has a main lobe around $r_s$ with nulls and sidelobes at voxel locations farther from $r_s$. The voxel grid spacing in CS-PAM in the axial and lateral directions should be chosen so that the voxels adjacent to $r_s$ have $f(\rho) \approx f(r_s)/2$. This process is repeated for different source locations $r_s$ in the region of interest to find a grid spacing that is adequate for the entire region, or the grid spacing may be non-uniform over the region if needed. The axial resolution is determined by the number of frequency bins (larger bandwidth implies better axial resolution) and the lateral resolution is determined by the array aperture (larger aperture implies better lateral resolution). Note that (32) also depends on the power spectrum of the source signal at the chosen frequency bins $|[\Xi]_k|^2$. These values may be set to 1 for simplicity, or more realistically for CS-PAM they may be computed from a model for the cavitation bubble waveform induced by HIFU insonification.

This approach may be extended to include the compression over frequency bins and sensors in order to choose the dimensions of the compressive sampling matrices ($M_F$ and $M_L$) in (19) and (20). In this case (19) and (20) are computed using $\Xi_i$ in (31) and $\Psi_i(\rho)$ in (32) to produce $\beta_m$ and $A_m(\rho)$, and then the inner product in (33) is modified to $$f(\rho) = \beta^T A(\rho) \qquad (34)$$

where $\beta$ and $A(\rho)$ are formed by the stacking operation in the line after (21). The objective is to choose $M_F$ and $M_L$ as small as possible to maximize the compression while also ensuring that $f(\rho)$ in (34) retains the mainlobe structure for voxel locations $\rho$ that are close to $r_s$. If the mainlobe structure is lost then the compressed data does not retain enough information to localize the source.

Referring to FIG. 2, an ultrasound system 200 according to an embodiment of the invention may comprise a geometrically focused ultrasound transducer 201, with an array of ultrasound transducer elements 202 positioned in an aperture 203 in the centre of the transducer 201. Each of the transducer elements 202 may be operable to generate ultrasound and also to detect ultrasound. They may therefore be usable in an active mode in which they generate and detect ultrasound to generate reflective (e.g. B-mode) ultrasound images, or in a passive mode in which they only detect ultrasound. The array may be a linear or convex linear array extending primarily in a direction which will be referred to as the x direction as shown in FIG. 2. The direction, perpendicular to the x direction, along the axis of the transducer will be referred to as the z direction. The imaging plane of the array is therefore the x-z plane. The direction perpendicular to both the x and z directions will be referred to as the y direction.

A control unit 204 is arranged to control generation of ultrasound signals by each of the transducer elements 202 and to receive the detection signals from each of the transducer elements 202. The control unit 204 may comprise a pre-amplifier and filter block 206 and an oscillator 208. The control unit 204 is also arranged to control the transducer 201 to control the power and frequency of the ultrasound generated by the transducer 201, for example using a signal from the oscillator 208 to control the frequency of the ultrasound. It will be appreciated that the control unit 204, while being described functionally, can be made up of a single processor, or two or more separate processors performing different functions, for example control and analyzing functions, within the system. The control unit is connected to a display screen 210 on which data derived from the detection signals can be displayed in a suitable format. In this case, the therapeutic transducer 201 has a focus in a focal region 214, in which it will generate the highest intensity ultrasound.

While the arrangement of FIG. 2 can be implemented using a variety of components and systems, in one embodiment an ultrasound data acquisition system may be used that allows simultaneous raw radio-frequency (RF) data or in-phase quadrature (I/Q) data—which can be demodulated to RF—across a wide ultrasound bandwidth (e.g. 1-15 MHz) from multiple individual elements 202. If the array is to be used in the passive mode, pulse transmission may be switched off so that the array acts on receive only. In some modes, one group of transducer elements 202 is used in the active mode and another group in the passive mode so that active and passive detection can be used simultaneously. To make the system clinically applicable, a therapeutic ultrasound transducer 201 may be used, which has a central aperture 203 for a linear (straight or convex) detector array 202.

Referring to FIGS. 3 and 4, the control unit 204 may be arranged to control the transducer elements 202 as a phased array. For example the control unit maybe arranged to generate a transmit signal for each of the transducer elements 202 to control the frequency and timing, i.e. relative phase, of the vibration, and hence the ultrasound, that each transducer element produces. Typically the frequency of vibration of each of the transducer elements is controlled so as to be the same, and the phase, or timing, of each of the elements is varied so as to steer the ultrasound that is generated by the array as a whole. The transducer elements may be arranged to vibrate in phase with each other, which produces ultrasound having straight parallel wave fronts 220 all travelling in the same direction, as shown in FIG. 2. This is suitable for anatomical ultrasound (B-mode or other reflective) imaging. If the phase of the vibrations of the elements 202 is shifted so that those at the outer ends of the array are in phase with each other, and the delay increase towards the centre of the array, as shown in FIG. 3, then this generates ultrasound with curved wave fronts 222 that converge at a focal region 224.

It will be appreciated that rather than having a separate transducer 201 for the focused ultrasound transmission, the array of ultrasound elements 204 may be used to generate ultrasound for both anatomical imaging and therapeutic FUS by switching rapidly between the two different phase configurations. Furthermore, since both anatomical ultrasound imaging and the passive acoustic mapping described above require detection of ultrasound reflected or generated by the tissue being imaged, this detection may also be done in some embodiments of the invention by the same transducer elements 202 that are used to transmit ultrasound. However that requires further time division and in many cases it is preferable to have a separate transducer array for detection, or receiving, of ultrasound. Therefore, in the following description where reference is made to transmit and receive arrays these will typically be separate arrays, but may alternatively be the same array.

Figure 5:
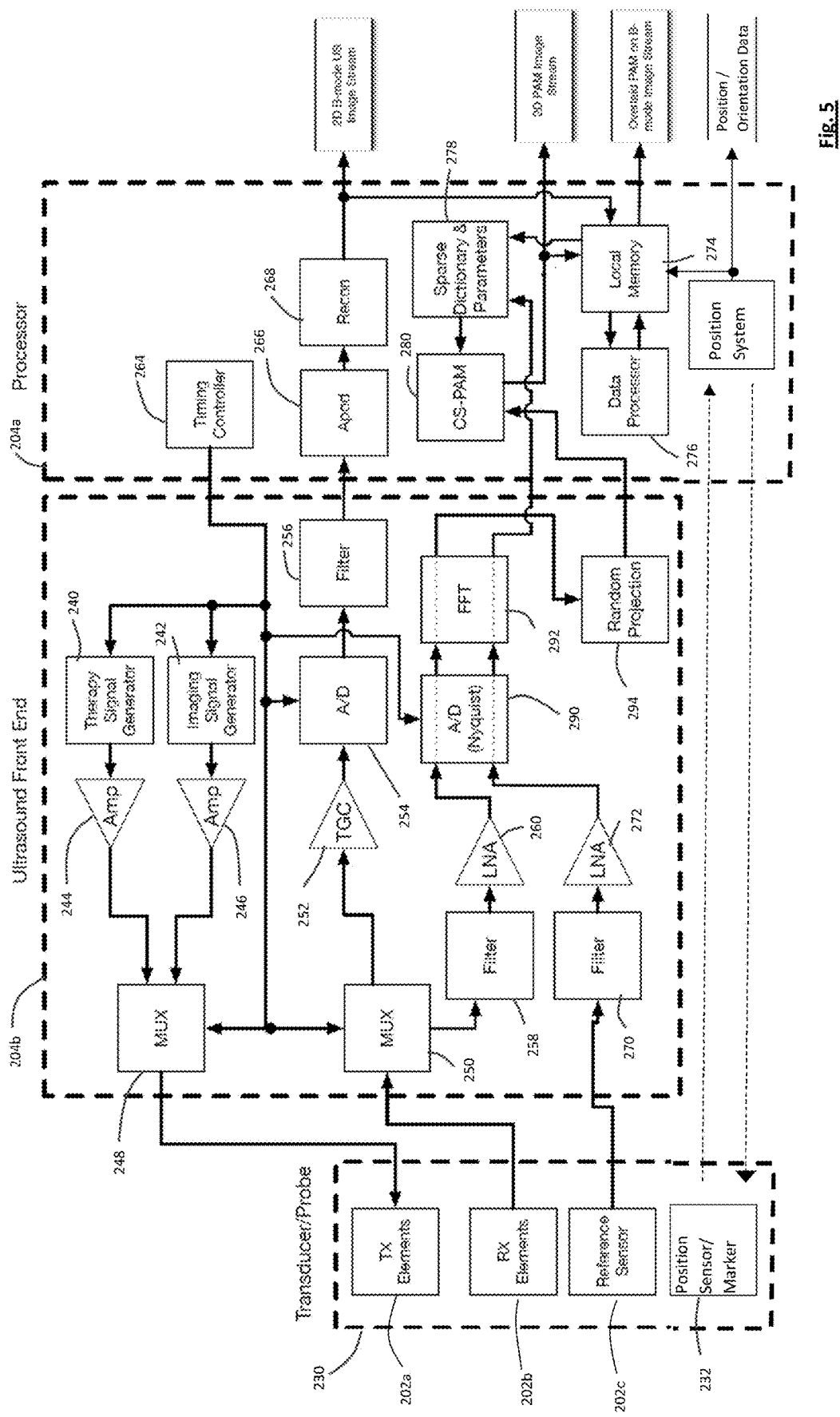
FIG. 5 is a functional block diagram of the system of another embodiment of the invention in which sensor signals are sampled in the time domain, transformed to the frequency domain and then compressed.

Referring to FIG. 5, in a practical implementation of the system, the transducer elements 202 are separated into two groups, each group of transducer elements being arranged in an array, a transmit array 202*a* and a receive array 202*b* and these are both mounted in a probe 230. Each of these arrays 202*a*, 202*b* may be a linear array as described above. One of the sensor elements is designated as a reference sensor 202*c*, which may for example be in the centre of the receive array 202*b*. The separate geometrically-FUS transducer 201 of FIG. 1 is therefore omitted. In a modification to this arrangement, the transducer elements are provided in a therapeutic group and an imaging group. The therapeutic group of transducer elements may then be arranged to generate focused ultrasound, while the imaging group of transducer elements are arranged to both transmit and receive the reflective imaging ultrasound, as well as to receive the passive cavitation mapping signals. The imaging group may be arranged to transmit flat planar ultrasound waves, or focused ultrasound, for example with sub-groups of the transducer elements controlled to provide different respective focal points at a common focal depth, to give a good quality image at that depth.

The probe may further comprise a position sensor 232 suitable for any of a number of known position and orientation sensing systems. For example it may be the sensor of an electromagnetic motion tracking system, it may comprise one or more markers enabling the position of the probe to be tracked with a stereoscopic optical camera, and infra-red camera, or a laser tracker.

The control unit 204 comprises a main processor 204*a* and an ultrasound front end processor 204*b*. The ultrasound front end 204*b* comprises a transmit side and a receive side. On the transmit side it comprises generators arranged to generate each of the ultrasound signals that are to be transmitted by the transmit array 202*a*. For example these may comprise a therapy signal generator 240 and an imaging signal generator 242. Each of these signal generators 240, 242 is arranged to output transmit signals that are input to the individual transducer elements of the transmit array 202*a* so that they transmit an ultrasound signal in the required form for therapeutic FUS and for B-mode ultrasound imaging respectively, for example as shown in FIGS. 2 and 3. The ultrasound front end 204*b* further comprises two amplifiers 244, 246 each arranged to amplify the transmit signals from a respective one of the signal generators 240, 242, and a multiplexer 248 which is arranged to receive both of the amplified transmit signals and send each of them to the correct transmit array 202*a* at the appropriate time in a time divisional multiplexed manner. A timing controller 264, which forms part of the main processor 204*a*, sends out trigger or synchronization signals to arrange the timing of the signal generators and multiplexers as will be described in more detail below.

The receive side of the ultrasound front end 204*b* comprises a multiplexer 250 arranged to receive all of the detection signals from the receive array 202*b* and separate out the anatomical ultrasound imaging signals (e.g. B-mode) from the passive acoustic mapping signals onto an anatomical ultrasound imaging channel and a PAM channel. This separation is done on the basis of timing, as the received anatomical imaging signals are reflections of the transmitted anatomical imaging signals, and the received PAM signals are generated by cavitation which is caused by the transmitted FUS signals. The anatomical imaging signals are time gain compensated by a TGC module 252, digitized by an ADC 254 and filtered by a digital filter 256. The PAM signals are filtered by an analogue filter 258 to isolate the high frequency broadband signals used for PAM, and amplified by a low noise amplifier 260.

The receive side of the ultrasound front end 204*a* further comprises another filter 270 arranged to filter the output signal from the reference sensor 202*c* to isolate the high frequency broadband signals used for PAM, a low noise amplifier 272 arranged to amplify the output from the filter 270.

The filtered and amplified outputs from each of the main array of sensor elements and the reference sensor are all input to an ADC 290 which is arranged to sample each of the signals at a series of sample points in the time domain at the Nyquist rate and output the digitized signals. An FFT module 292 receives those digitized signals and, for each sample period, converts them to the frequency domain. A random projection module 261 receives the frequency components from each of the sensor signals and performs the selection of those frequency components for compression of the sensor data.

The FFT data from the reference sensor signal is input to the sparse dictionary and parameters unit 278 and the FFT data from the main sensor array is input to the random projection unit 294 which performs the selection of the frequency components from each of the sensor signals in similar manner to the random projection unit 261 in FIG. 5 except that it operates on digital signals.

This may be done in hardware using filter components and integrators which integrate each of the sensor data over each sample period. The values after integration are then sampled and digitized by an ADC 262, once for each sample period.

A high rate ADC 274 is arranged to sample the filtered reference sensor signal at each of the sample frequencies, to enable construction of the frequency domain basis.

The main processor 204a comprises the timing controller 264 which is arranged to provide timing inputs to the ultrasound signal generators 240, 242, the multiplexers 248, 250 and the ADCs 254, 262 as described above. The timing inputs to the ultrasound signal generators 240, 242 are arranged to trigger the generation of the therapeutic FUS signal and the anatomical ultrasound imaging signal in an alternating manner, each for a respective series of brief time periods. The multiplexer 248 uses the timing signal it receives from the timing controller 264 to multiplex the two types of ultrasound generation signal onto the control input to the transmitter array 202a, so that the transmitter array 202a will generate alternating pulses of therapeutic FUS and focused or unfocused imaging ultrasound. The receive multiplexer 250 is controlled by the timing controller 264 to switch the signals from the receive array 202b between the B-mode channel and the PAM channel based on the time of transmission of the two different types of ultrasound and the known or assumed delay between transmission and reception of the relevant ultrasound signals. The timing controller 264 also provides timing inputs to the ADCs 254 262 to control the sampling rate of the analogue signals by the ADCs.

The main processor 204a further comprises an apodization unit 266 and an image reconstruction unit 268 which are arranged to receive the filtered digital signals from the B-mode channel of the ultrasound front end 204b and generate from them an anatomical ultrasound image, for example in the form of a 2D B-mode ultrasound imaging stream which may comprise a sequence of time stamped 2D image frames.

The main processor 204a further comprises a sparse dictionary and parameters unit 278 and a PAM imaging unit 280. The sparse dictionary and parameters unit 278 is arranged to receive the digitized frequency domain reference signals from the FFT unit 292, and to generate from that the sparse basis dictionary (compressed dictionary) defined in equation (19). The PAM imaging unit 280 is arranged to receive the compressed data signals from the random projection unit 294, and the sparse dictionary from the sparse dictionary and parameters unit 278, and generate from them a PAM image, for example in the form of a 2D PAM imaging stream with one image frame for each sample period.

The main processor 204a further comprises a local memory 274 and a data processor 276. The local memory 274 is arranged to receive and store the image streams from the anatomical and PAM imaging channels. It is also arranged to receive and store 3D anatomical image data obtained from a previous scan of the patient, for example in the form of a set of 2D image slices obtained by CT or MRI scanning, which may be in DICOM format for example. The data processor 276 is arranged to process the data stored in the local memory so as to generate a combined image or image stream in which the PAM image of the FUS-induced cavitation is superimposed on an a 3D anatomical image of the patient, which may be the pre-scanned 3D image, or may be a 3D ultrasound image generated from the compounded 2D B-mode ultrasound image slices. The processing method by which the combined image may be obtained is not relevant to the present invention and will not be described.

Figure 6:
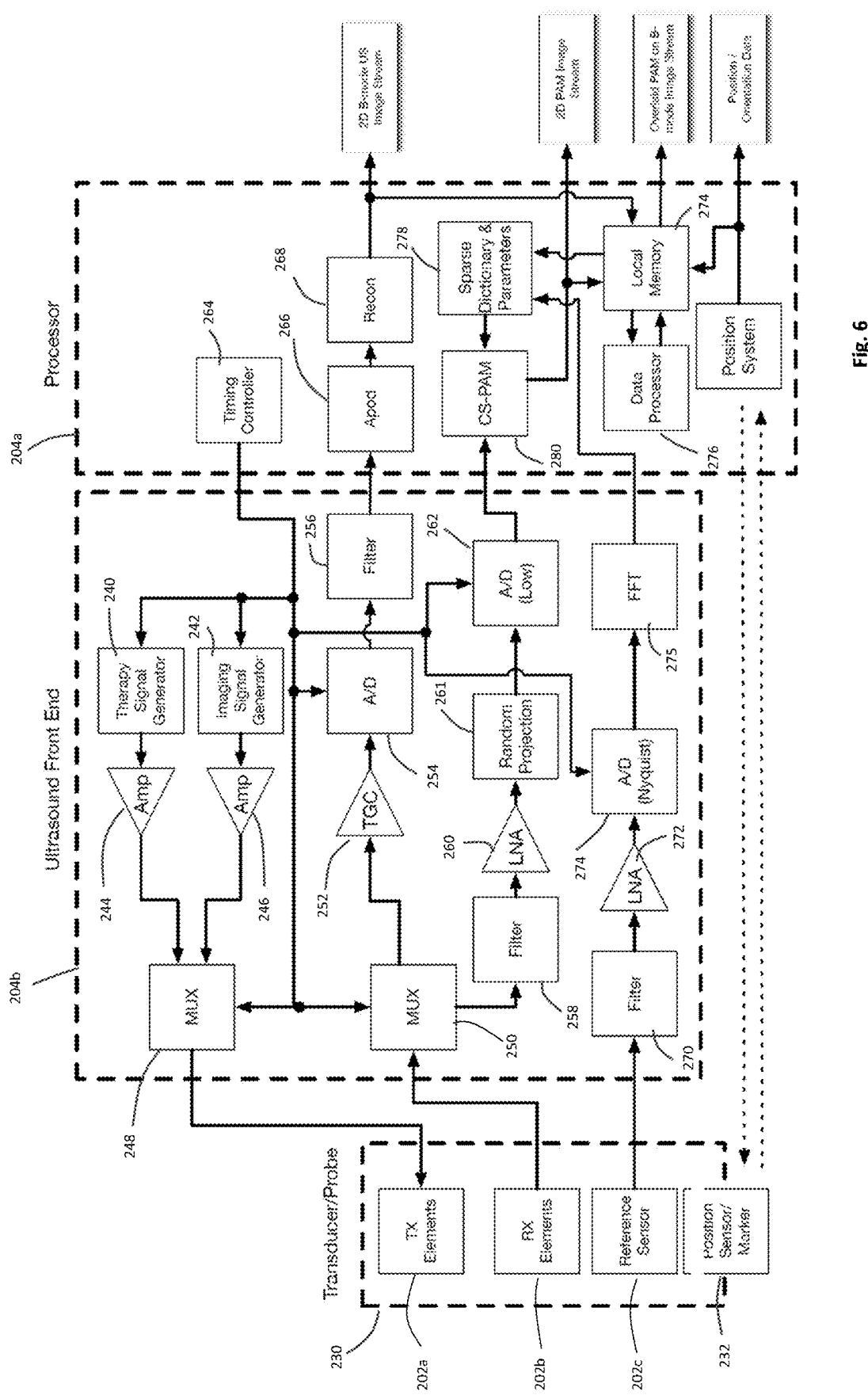
FIG. 6 is a functional block diagram of the system of a further embodiment of the invention in which sensor signals are sampled in the frequency domain.

Referring to FIG. 6, in a modification to the embodiment of FIG. 5, the sensor signals are sampled in the frequency domain. Components of this embodiment that correspond to those in FIG. 5 are indicated by the same reference numerals and will not be described in detail. The random projection unit 261 is arranged to receive the amplified sensor output signals from each of the sensor elements 202b, filter and compress them as discussed above with reference to equation (27) and the integrations in (27) are sampled by an ADC 262 at the image frame rate. These compressed samples are then input to the CS-PAM unit 280. A separate ADC 274 is arranged to sample the RS signal data at full Nyquist rate and an FFT unit 275 transforms that data to the frequency domain for all of the frequency bins and the frequency domain reference data is input to the sparse dictionary and parameters unit 278.

In a further embodiment the sensors signals including the reference signal are sampled in the time domain, there is no FFT conversion to the frequency domain, and the basis is constructed in the time domain as described above in equation (14) and the voxel positions determined by the minimization accordingly. The system for this method would have components corresponding to those of FIG. 6 except that the FFT unit 275 would be omitted and the reduced sampling of the sensor signals would be done in the time domain, and the compressed dictionary would be defined in the time domain.

Referring to FIGS. 7 to 9, the system of FIG. 2 to 5 or 6 may be incorporated in various different probe configurations. For example, referring to FIG. 6, the probe 230 may be connected to an electronically, or manually, controlled movement control system 600, such as a robotic arm or multi-axis movement system, arranged to support the probe and control its movement in six degrees of freedom (three along orthogonal translational directions of movement and three about orthogonal rotational axes) in response to input from an electronic control system or manual inputs. In this case the position and orientation of the probe 230 may be determined from a position sensor 632 mounted on the probe as described above, or may be determined from the operation of the movement control system.

Referring to FIG. 7, the probe may be a hand-held external probe 730 having a contact surface 700 arranged to be placed in contact with the patient's skin, and with the transmit and receive arrays 702a, 702b mounted in or adjacent to the contact surface 700. In this case the position sensor 732 is mounted in the or fixed onto the body of the probe 730 so that all manual movements of the probe can be recorded.

Referring to FIG. 8, the probe may be a hand-held internal or intra-operative probe 830 having a contact surface 800 arranged to be placed in contact internally to the patient, and with the transmit and receive arrays 802a, 802b mounted in or adjacent to the contact surface 800. In this case again the position sensor 832 is mounted in the body of the probe 830 so that all manual movements of the probe can be recorded as described above.

Referring to FIG. 10, rather than all being mounted on a common probe, the system may comprise separate probes each with a different group of the transducer elements supported on it. For example the system may comprise an anatomical imaging probe 900 having an array 902 of transducer elements supported on it. This array 902 may be a linear or convex array and may be arranged to transmit the reflective imaging ultrasound, for example a shown in FIG. 2, and to receive the reflected ultrasound, either using the same group of transducer elements within the array 902, or a different group of transducer elements within the array 902, or using a separate array of transducer elements. The system may comprise a FUS probe 904 having an array 906 of transducer elements arranged to generate therapeutic FUS for example as shown in FIG. 3. The system may further comprise a PAM probe 908 having an array 910 of transducer elements arranged to receive. Each of the probes 900, 904, 908 further comprises a position sensor 912, 914, 916 so that the position of the probe, and hence the transducer arrays mounted on it, can be monitored. The system can then operate in the same way as the systems described above except that the calibration step 300 used to spatially align the PAM image with the anatomical ultrasound image is replaced by a transformation which varies with time and is determined for each image frame of the PAM image stream based on the relative positions of the two probes 900, 908.

In a further embodiment, the system comprises a FUS ultrasound transmitter mounted on a probe or a robot arm, and a movable probe which has the PAM imaging receive transducer elements and both the transmit and receive elements of the anatomical ultrasound imaging system on it, either as separate arrays or as a single common array, or as a transmit array for the anatomical ultrasound imaging and a receive array for both the PAM imaging and the anatomical ultrasound imaging.

A simulation of the system of FIG. 5 was run using various different PAM methods, in particular using a curvilinear array with L=128 elements and a voxel grid with N=2,626 locations (101 lateral×26 axial, 40 mm×40 mm area). For CS PAM compression ratios of ~2% were used: CS-PAM uses only 2% of the data processed for conventional PAM. The other methods used in the simulation were standard beamforming (SB), standard Capon Beamforming (SCB) and robust Capon Beamforming (RCB).

For the simulation of CS-PAM: MF=300, ML=32, solving optimization with perturbed orthogonal matching pursuit (POMP).

Figure 11:
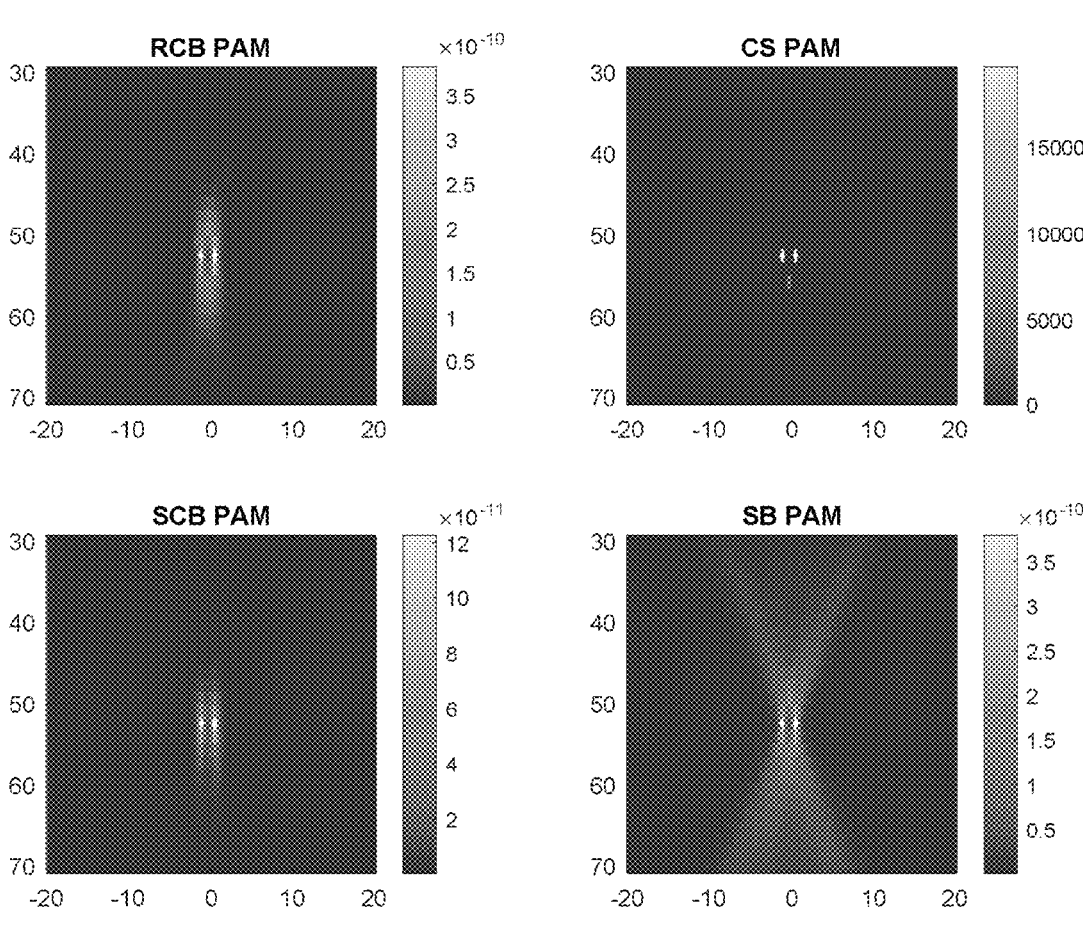
FIG. 11 shows simulated results of the CS PAM method being used to image two sources.

For all simulations bubble signals were generated with random pulse train bubble model, SNR 40 dB, and resolution was evaluated using 2 bubble sources, performance evaluated with bubble clouds, on and off grid (on-grid shown in FIG. 11) from which it can be seen that the simulation using CS PAM has significantly less artifacts than the other methods.

Figure 12:
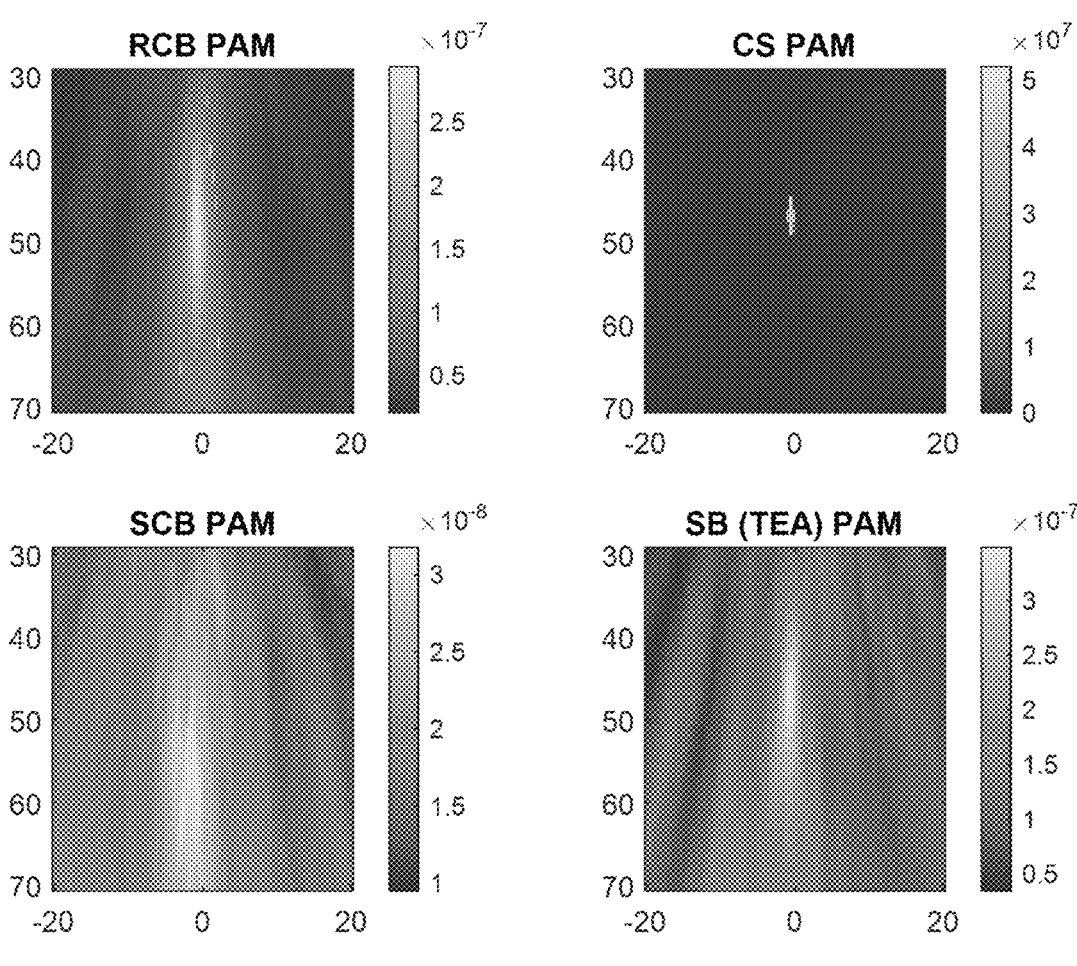
FIG. 12 shows results of the CS PAM method being used in vivo in porcine liver to image a single source.

In vivo treatment of porcine liver using SonoTran Particles was also carried out, the results of which are shown in FIG. 12 for a single region of cavitation. Again CS PAM has significantly less artifacts than the other methods.

The invention claimed is:

1. A near field passive compression wave imaging system for locating cavitation bubbles, the system comprising a plurality of sensor elements arranged in an array and each arranged to produce an output signal representing detected compression waves, and a processor configured to:

define a sample period, and a sample space over which the signal can be sampled at each of a plurality of sample points in the sample space;

define a grid of candidate cavitation bubble positions;

define a random projection identifying a respective different group of the sample points for each of the output signals;

sample each of the output signals at the group of sample points defined by the random projection to generate sample data;

define a dictionary which defines sample values that would be obtained for the signal of each of the respective group of sensor elements at each of the sample points for the sample period for a cavitation bubble at each of the candidate cavitation bubble positions;

define a vector, the vector having a plurality of elements each having a value, wherein the values of the elements identify at which of the candidate cavitation bubble positions a cavitation bubble is located;

perform a minimization operation to derive the vector element values, and hence the cavitation bubble positions, from the sample data, the dictionary and the random projection.

2. The system according to claim 1 wherein the sample space is time and the processor is further configured to define a sample rate that defines the sample points as a plurality of sample times within the sample period at which samples can be taken.

3. The system according to claim 1 wherein the sample space is frequency.

4. The system according to claim 3 wherein the processor is further configured to define the sample points as a plurality of sample frequencies at which samples can be taken.

5. The system according to claim 3 wherein the processor is configured to separate out an analogue component of the sensor output signals at each of the frequency sample points, and to sample each of the components for the sample period.

6. The system according to claim 2 wherein the processor is configured to sample each of the sensor output signals, and to determine frequency component samples for each of the output signals from the time sample space.

7. The system according to claim 1 wherein the processor is configured to form linear combinations of the sample data from the sensors thereby to form virtual sensor data corresponding to a plurality of virtual sensors.

8. The system according to claim 1 wherein the random projection is defined by at least one matrix.

9. The system according to claim 1 wherein the processor is configured to identify one of the sensor elements as a reference sensor element, to sample the output signal from the reference sensor element at each of the sample points to generate reference data, to define a delay time for each combination of one of the candidate cavitation bubble positions and one of the senor elements, and to determine the dictionary from the reference data and the delay times.

10. A method of near field passive compression wave imaging of cavitation bubbles, the method comprising:

receiving a plurality of output signals representing detected compression waves each from a respective sensor element in an array of sensor elements;

defining a sample period, and a plurality of sample points over a sample space;

defining a grid of candidate cavitation bubble positions;

defining a random projection identifying a respective different group of the sample points for each of the output signals;

sampling each of the output signals at the group of sample points defined by the random projection to generate sample data;

defining a dictionary which defines sample values that would be obtained for a signal of each of the sensor elements at each of the respective group of sample points for the sample period for a cavitation bubble at each of the candidate cavitation bubble positions;

defining a vector, the vector having a plurality of elements each having a value, wherein the values of the elements identify at which of the candidate cavitation bubble positions a cavitation bubble is located; and performing a minimization operation to derive the vector element values, and hence the cavitation bubble positions, from the sample data, the dictionary and the random projection.

11. The method according to claim 10 wherein the sample space is time, the method further comprising defining a sample rate that defines the sample points as a plurality of sample times within the sample period at which samples can be taken.

12. The method according to claim 10 wherein the sample space is frequency.

13. The method according to claim 12 further comprising defining the sample points as a plurality of sample frequencies at which samples can be taken.

14. The method according to claim 12 further comprising separating out an analogue component of the sensor output signals at each of the frequency sample points, and sampling each of the components for the sample period.

15. The method according to claim 11 further comprising sampling each of the sensor output signals, and determining frequency component samples for each of the output signals from the time sample space.

16. The method according to claim 10 further comprising forming linear combinations of the sample data from the sensors thereby to form virtual sensor data corresponding to a plurality of virtual sensors.

17. The method according to claim 10 wherein the random projection is defined by at least one matrix.

18. The method according to claim 10 further comprising identifying one of the sensor elements as a reference sensor element, sampling the output signal from the reference sensor element at each of the sample points to generate reference data, defining a delay time for each combination of one of the candidate cavitation bubble positions and one of the senor elements, and determining the dictionary from the reference data and the delay times.

19. A near field passive compression wave imaging system for locating cavitation bubbles, the system comprising a plurality of sensor elements arranged in an array and each arranged to produce an output signal representing detected compression waves, and a processor configured to:

define a sample period, and a sample space over which the signal can be sampled at each of a plurality of sample points in the sample space;

define a grid of candidate cavitation bubble positions;

define a random projection identifying a respective different group of the sample points for each of the output signals;

sample each of the output signals at the group of sample points defined by the random projection to generate sample data;

define a dictionary which defines sample values that would be obtained for the signal of each of the respective group of sensor elements at each of the sample points for the sample period for a cavitation bubble at each of the candidate cavitation bubble positions;

define, for each of the sensor elements, a vector, the vector having a plurality of vector elements each having a value, wherein the values of the vector elements identify at which of the candidate cavitation bubble positions a cavitation bubble is located; and perform a minimization operation to derive the vector element values, and hence the cavitation bubble positions, from the sample data, the dictionary, and the random projection.

20. A method of near field passive compression wave imaging of cavitation bubbles, the method comprising:

receiving a plurality of output signals representing detected compression waves each from a respective sensor element in an array of sensor elements;

defining a sample period, and a plurality of sample points over a sample space;

defining a grid of candidate cavitation bubble positions;

defining a random projection identifying a respective different group of the sample points for each of the output signals;

sampling each of the output signals at the group of sample points defined by the random projection to generate sample data;

defining a dictionary which defines sample values that would be obtained for a signal of each of the sensor elements at each of the respective group of sample points for the sample period for a cavitation bubble at each of the candidate cavitation bubble positions;

defining, for each of the sensor elements, a vector, the vector having a plurality of vector elements each having a value, wherein the values of the vector elements identify at which of the candidate cavitation bubble positions a cavitation bubble is located; and performing a minimization operation to derive the vector element values, and hence the cavitation bubble positions, from the sample data, the dictionary and the random projection.

* * * * *